(12) United States Patent
Moissl et al.

(10) Patent No.: US 10,092,685 B2
(45) Date of Patent: Oct. 9, 2018

(54) METHOD, APPARATUS, AND DEVICE FOR CALCULATING OR APPROXIMATING ONE OR MORE VALUES REPRESENTING PARAMETERS OF A PATIENT

(75) Inventors: Ulrich Moissl, Karben (DE); Sebastian Wieskotten, Ober-Ramstadt (DE); Paul Chamney, Herts (GB); Volker Nier, Reichelsheim (DE); Peter Wabel, Darmstadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 704 days.

(21) Appl. No.: 13/991,710

(22) PCT Filed: Dec. 9, 2011

(86) PCT No.: PCT/EP2011/006220
§ 371 (c)(1),
(2), (4) Date: Jul. 10, 2013

(87) PCT Pub. No.: WO2012/076184
PCT Pub. Date: Jun. 14, 2012

(65) Prior Publication Data
US 2013/0277287 A1 Oct. 24, 2013

Related U.S. Application Data

(60) Provisional application No. 61/421,224, filed on Dec. 9, 2010.

(30) Foreign Application Priority Data

Dec. 9, 2010 (EP) .................................. 10015466

(51) Int. Cl.
*B01D 21/30* (2006.01)
*B01D 61/00* (2006.01)
(Continued)

(52) U.S. Cl.
CPC ............ *A61M 1/16* (2013.01); *A61M 1/1613* (2014.02); *G06F 19/34* (2013.01);
(Continued)

(58) Field of Classification Search
CPC .... A61M 1/16; A61M 1/1613; A61M 1/1656; A61M 1/00; A61M 5/00; B01D 21/30;
(Continued)

(56) References Cited

U.S. PATENT DOCUMENTS

| 5,230,702 A | 7/1993 | Lindsay et al. |
| 2005/0102165 A1* | 5/2005 | Oshita ..................... A61M 1/14 705/3 |

(Continued)

FOREIGN PATENT DOCUMENTS

| EP | 1 364 666 A1 | 11/2003 |
| EP | 1872811 | 1/2008 |

(Continued)

OTHER PUBLICATIONS

Flythe et al. (Rapid fluid removal during dialysis is associated with cardiovascular morbidity and mortality, Kidney Intl., 79(2), pp. 250-257 (Jan. 2011)).*

(Continued)

*Primary Examiner* — Hayden Brewster
(74) *Attorney, Agent, or Firm* — Fish & Richardson P.C.

(57) ABSTRACT

A method for calculating or estimating or approximating one or more values representing parameters of a patient includes the step of interpolating or extrapolating of at least one later value of a first parameter taking into account at least one earlier value of the first parameter, at least one earlier and at least one later value of a second parameter, and a mathematical relation between the first and the second parameter.

(Continued)

An apparatus, a blood treatment device, a digital storage device, a computer program product, and a computer program are also described.

19 Claims, 16 Drawing Sheets

(51) Int. Cl.
    *A61M 1/16*     (2006.01)
    *G06F 19/00*     (2018.01)
    *G16H 50/50*     (2018.01)
    *C02F 9/00*     (2006.01)
    *B01D 65/00*     (2006.01)
    *B01J 49/00*     (2017.01)
    *A61M 5/00*     (2006.01)
    *A61M 1/00*     (2006.01)

(52) U.S. Cl.
    CPC ......... *G06F 19/3481* (2013.01); *G16H 50/50* (2018.01); *A61M 2205/52* (2013.01)

(58) Field of Classification Search
    CPC ........ B01D 61/00; B01D 61/08; B01D 61/12; B01D 61/22; B01D 61/32; B01D 65/00; B01J 49/00; C02F 1/283; C02F 1/32; C02F 1/42; C02F 1/441; C02F 1/66; C02F 1/78
    USPC ..... 210/85, 87, 88, 96.1, 96.2, 97, 138, 143, 210/321.6, 646, 650, 739; 604/65, 67; 702/19
    See application file for complete search history.

(56) References Cited

U.S. PATENT DOCUMENTS

| | | | |
|---|---|---|---|
| 2006/0025931 A1* | 2/2006 | Rosen | G06F 19/345 702/19 |
| 2006/0226079 A1* | 10/2006 | Mori | A61M 1/16 210/646 |
| 2006/0289342 A1 | 12/2006 | Sugioka et al. | |
| 2007/0112289 A1* | 5/2007 | Cavalcanti | A61M 1/3621 604/4.01 |
| 2008/0067132 A1 | 3/2008 | Ross et al. | |
| 2008/0071147 A1* | 3/2008 | Chamney | A61B 5/0537 600/300 |
| 2011/0036773 A1* | 2/2011 | Moissl | A61M 1/3639 210/646 |

FOREIGN PATENT DOCUMENTS

| | | |
|---|---|---|
| JP | H09500721 A | 1/1997 |
| JP | 9-99061 | 4/1997 |
| JP | 2004248793 A | 9/2004 |
| JP | 2006288625 | 10/2006 |
| JP | 2009172442 A | 8/2009 |
| JP | 2009183558 | 8/2009 |
| JP | 2010531678 A | 9/2010 |
| JP | H5329204 | 10/2013 |
| WO | 1992/019153 A1 | 11/1992 |
| WO | 9427695 | 12/1994 |
| WO | 2000/066197 A1 | 11/2000 |

OTHER PUBLICATIONS

PCT International Search Report from PCT/EP2011/006220, dated Feb. 2, 2012.

* cited by examiner

METHOD, APPARATUS, AND DEVICE FOR CALCULATING OR APPROXIMATING ONE OR MORE VALUES REPRESENTING PARAMETERS OF A PATIENT

CROSS REFERENCE TO RELATED APPLICATIONS

The present application is the national stage entry of International Patent Application No. PCT/EP2011/006220, filed on Dec. 9, 2011, which claims priority to European Application No. EP 100 15 466, filed on Dec. 9, 2010, and claims priority to U.S. Provisional Patent Application Ser. No. 61/421,224, filed on Dec. 9, 2010.

FIELD OF INVENTION

The present invention relates to a method for calculating or estimating or approximating one or more values representing parameters of a patient, the method comprising the step of interpolating or extrapolating of at least one later value of a first parameter taking into account at least one earlier value of the first parameter, at least one earlier and at least one later value of a second parameter, and a mathematical relation between the first and the second parameter. It further relates to an apparatus, a blood treatment device, further to a digital storage device, a computer program product, and a computer program.

BACKGROUND INFORMATION

For the extracorporeal treatment of blood and further applications, it is of value to know the value of one or more of the patient's parameters in advance. This knowledge may contribute to setting or controlling the treatment machine in a more appropriate manner. For example, knowing the patient's overhydration before setting the ultrafiltration rate or volume may provide for certain advantages. For instance, patients who are treated at an ultrafiltration rate (UFR) that has been set (too) high are likely to collapse during, e.g., dialysis because of the amount of fluid withdrawn from their vessel system by the treatment. Patients who are treated at an ultrafiltration rate (UFR) that has been set (too) low are likely to unnecessarily spend time at the treatment site (hospital, clinic or even at home bound to the treatment machine), or, worse, to be sent home again without having reduced their overhydration (OH) level to an appropriate extent. Regrettably, actual or to-date values are not always available for the parameters of interest at the beginning of a blood treatment session.

SUMMARY

By means of the present invention, a method for calculating or estimating or approximating one or more values representing parameters of a patient which are missing or which have not been measured recently is suggested. Also, an apparatus for carrying out the method according to the present invention is provided, as well as a device comprising the apparatus, a digital storage device, a computer program product, and a computer program.

Accordingly, in one aspect of the present invention, the method for calculating or estimating or approximating one or more values representing one or more parameters of a patient comprises the step of interpolating or extrapolating of at least one later value of a first parameter (and possibly of further parameters as well) taking into account at least one earlier value of the first parameter (and possibly of further parameters as well), at least one earlier and at least one later value of a second parameter (and possibly of further parameters as well), and a mathematical relation between the first and the second parameter.

The patient can be either a human being or an animal. The patient may be sound or ill. The patient may be in need of medical care or not.

Accordingly, in another aspect of the present invention, the apparatus is configured to carry out the method according to the present invention.

Accordingly, in another aspect of the present invention, the blood treatment device comprises at least one apparatus according to the present invention.

Accordingly, in another aspect of the present invention, the digital storage device, in particular a disc, CD or DVD, flash memory, USB memory, or the like has electrically readable control signals which are able to interact with a programmable computer system such that a method according to the present invention will be executed.

Accordingly, in another aspect of the present invention, the computer program product has a program code stored on a machine readable data medium for executing a method according to the present invention when executing the program product on a computer.

Accordingly, in another aspect of the present invention, the computer program has a program code for the execution of a method according to the present invention when executing the program on a computer.

Exemplary embodiments can include one or more of the following features.

In some exemplary embodiments according to the present invention, the values to be estimated, calculated or approximated are vital parameters of the patient. The parameters may be variable over time (e.g., in the course of days, weeks, etc.).

In certain exemplary embodiments according to the present invention, the term 'later value' relates to a missing value, or to a value that is to be approximated or calculated or estimated.

In some exemplary embodiments according to the present invention, the term 'later value' means a value that relates to a later (as regards to time) state of the patient than the earlier value.

In certain exemplary embodiments according to the present invention, the later value of the first parameter refers to the very same state of the patient as does the later value of the second parameter. For example, in these exemplary embodiments both the later value of the weight and the later value of overhydration relate to the physical state of the patient of one particular moment (e.g., at the beginning of the dialysis treatment session).

In some exemplary embodiments according to the present invention, the later value of the first parameter does not refer to the very same state of the patient as the later value of the second parameter. For example, in these exemplary embodiments both the later value of the weight and the later value of overhydration relate to two possibly different physical states of the patient of two particular moments (e.g., the later value of weight may relate to November 25 whereas the later value of the overhydration may relate to November 24 or November 26).

It is noted that everything that is stated above with regards to the term 'later value' may in particular exemplary embodiments according to the present invention be also true for the term 'earlier value'.

In some exemplary embodiments according to the present invention, an 'earlier' value of one particular parameter describes the parameter (or its value) at a first point of time, whereas the 'later' value of the particular parameter describes or is believed to describe that parameter (or its value) at a second point of time with the second point of time occurring after the first point of time. It is noted the there is not necessarily just one 'earlier' value. Rather, more than one 'earlier' parameter can be contemplated as well.

In certain exemplary embodiments according to the present invention, the earlier value of a first parameter does not necessarily reflect the patient's state at the time when the earlier value of a second parameter has been measured, found or estimated. The same may be true for the 'later' point of time.

In certain exemplary embodiments, the method according to the present invention is contemplated or carried out with the intention to control a treatment of the blood of the patient. This can take place by, e.g., controlling or setting the blood treatment device according to the results found by means of the method according to the present invention.

In some exemplary embodiments, the values representing a parameter are values that describe the patient's state or aspects thereof at a certain point of time. That point of time may be hours or minutes before or right at the beginning of a blood treatment session.

In certain exemplary embodiments, the 'earlier' or 'older' value has been measured (or even obtained by means of the method according to the present invention) at or for a first or earlier point of time, whereas the 'later' or 'new' value has been measured or obtained by means of the method according to the present invention at or for a second or later point of time.

In certain exemplary embodiments of the method according to the present invention, the first, the second and optionally further parameters are selected from a group of parameters, the group comprising at least the haematocrit (HCT), the blood water content (BWC), the extracellular water content (EWC), the blood volume (BV), the blood volume at the beginning of a treatment session (BV_start), the normohydrated blood volume ($BV_0$), the overhydration (OH), the relative overhydration (relOH) (being defined as overhydration over extracellular water; OH/ECW), the normoweight (Normwgt), the preweight (before treatment), the postweight (after treatment), the haemoglobin mass (mass_Hb) or the haemoglobin concentration in blood (Hb).

In some exemplary embodiments, the method comprises the step of minimizing a mathematical error.

In certain exemplary embodiments of the present invention, the method comprises the step of minimizing of a square error, in particular a mean square error.

It is to be noted that in particular exemplary embodiments according to the present invention a square error is understood as a mathematical error. Further, any mathematical procedure described in here (such as minimizing a square error, weighting values, calculating means and the like) can be understood as minimizing a mathematical error.

In some exemplary embodiments according to present invention, the method comprises the step of weighting one or more of the earlier values (any one of them).

In certain exemplary embodiments according to the present invention, the method comprises the step of weighting values or mean values derived or calculated from estimated and/or measured earlier or older values (or means thereof) of one or more parameters.

In some exemplary embodiments, the method encompasses calculating a mean between estimated and measured earlier or older values of one or more parameters.

In some exemplary embodiments according to the present invention, the method comprises using a mathematical filter or an estimator or a predictor or a combination or sequence of filters, estimators or predictors, respectively. In these or in different exemplary embodiments, the method encompasses using a repression analysis or neuronal networks.

In certain exemplary embodiments of the present invention, the method comprises using a linear filter, in particular a Kalman filter. In others, a non-linear Kalman filter is used. The use of the latter is of particular advantage if the transition equations or the output equations are non-linear.

In exemplary embodiments in which a Kalman filter is used, the filter can be an unscented Kalman filter, a Kalman-Bucy filter, a hybrid Kalman filter, or an extended Kalman filter.

In certain exemplary embodiments, the filter used, and in particular the Kalman filter used (if a Kalman filter is used), is either a time-discrete or a time-continuous filter.

In some exemplary embodiments according to present invention, the method comprises using a filter that works partly or completely recursively.

In certain exemplary embodiments of the present invention, a filter is used that estimates the internal state of a linear dynamic system from a series of noisy measurements.

In some exemplary embodiments according to present invention, a linear quadratic estimator (in control theory) is used.

In certain exemplary embodiments of the present invention, a filter is used that in turn uses a predictor-corrector scheme to estimate the state of a dynamic process.

In some exemplary embodiments according to present invention, a combination of a process model and a measurement model is used, each model being formulated as stochastic difference equation, to estimate the (frequently not observable) inner state of the process; the combination may be a stochastic estimator.

In certain exemplary embodiments of the present invention, a (simple) recursive Bayesian estimator of a Markov process is used.

In some exemplary embodiments of the present invention, an efficient stochastic estimator is used to recursively calculate the not observable inner states of a physiological process, in particular a patient's state. In certain exemplary embodiments, an estimator is used that solves in a predictor-corrector scheme stochastic difference equations of a process-model using observable noisy measurements of the process. Possible implementations thereof include the linear Kalman filter (together with its non-linear modifications), regression analysis, and neural networks.

In certain exemplary embodiments, a discrete linear formulation of the model or filter used can be as follows:

Not observable state $x \in R^n$ of a discrete-time controlled process $$X_k = Ax_{k-1} + Bu_{k-1} + w_{k-1}$$

Observable measurements $z \in R^m$ $$z_k = Hx_k - v_k$$

k: current time step
$w_k, v_k$: process and measurement noise
A: state transition matrix ($A = A_k$ possible)
B: control input matrix ($B = B_k$ possible)
H: observation matrix ($H = H_k$ possible)

In some exemplary embodiments, a discrete non-linear formulation of the model or filter used can be as follows:

$$x_k = f(x_{k-1}, u_{k-1}) + w_{k-1}$$

and $$z_k = h(x_k) + v_k$$

with f,h being nonlinear functions.

In certain exemplary embodiments according to the present invention, the method comprises the step of controlling a device for treating a patient's blood in accordance with or based on the one or more values calculated.

In some exemplary embodiments, some or all of the steps of the method according to the present invention are carried out by means of corresponding devices (such as, e.g., an estimating device, an interpolation or extrapolation device, and the like). Such devices can explicitly be configured for carrying out the respective steps.

In certain exemplary embodiments of the present invention, the apparatus comprises an output device for outputting results provided by carrying out the respective method.

In some exemplary embodiments of the present invention, the apparatus is configured to control a device for treating a patient's blood in accordance with or based on the one or more values calculated or approximated or estimated by the method according to the present invention.

In certain exemplary embodiments of the present invention, the device is for treating a patient by means of dialysis.

In some exemplary embodiments of the present invention, the device is for treating a patient by haemofiltration, ultrafiltration, and/or haemodialysis.

In certain exemplary embodiments according to the present invention, one or more of the following advantages may be provided. For example, missing values may be provided although corresponding measurements did take place. Also, a weighting may provide for more appropriate estimators and, hence, for values closer to the real state.

Further, in some exemplary embodiments, the computational effort is low when compared to other approaches.

Besides, since the most weight is given to the value with the least uncertainty in certain exemplary embodiments, the estimates produced by the present invention tend to be closer to the true values.

Using the Kalman filter or similar filters or models may advantageously allow that it can proceed or operate even if no recently measured input value is available. Rather, such filters may use earlier values instead. Using appropriate and variable weights for computing values by means of a Kalman filter or similar filters allows for computing also on the basis of values that do not necessarily have to be real values, i.e., measured values. That way, the Kalman filter may rely on input values or parameters that have not been measured recently. This can be done with little effort.

Further, in certain exemplary embodiments the Kalman filter may provide additional information about internal state of the patient. These information relate, for example, to the in-fact blood volume, the Hb mass or any (other) parameters that cannot be measured in a direct or easy manner.

Other aspects, features, and advantages, and exemplary embodiments according to the present invention will be described herein with reference to the accompanying drawings.

DETAILED DESCRIPTION

In some of the accompanying drawings, 'relOH' (being defined as OH/ECW) or relAEOH are used, but the same graphics could be plotted with absolute OH.

Also, the time axis of some of the accompanying drawings is divided into months (with 01 standing for January, 05 standing for May of the same year, and so on).

Figure 1:
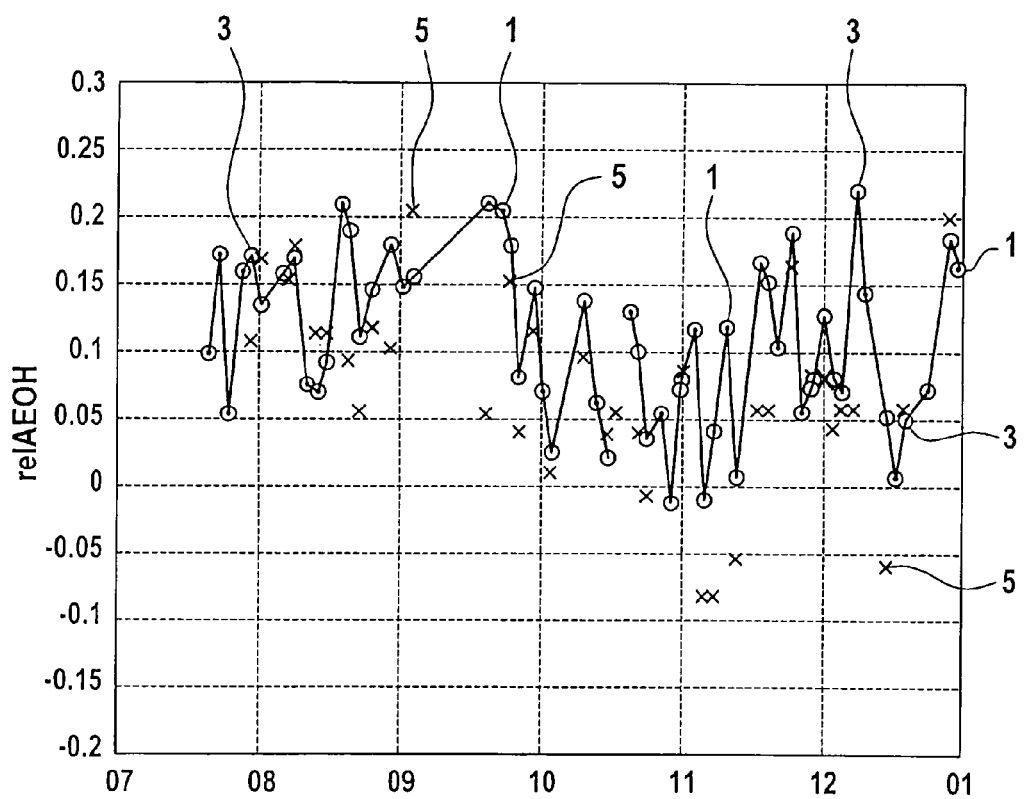
FIG. 1 shows an interpolation of the overhydration (OH) for blood treatment sessions which are not accompanied by contemporaneous measurements.

FIG. 1 shows the relative overhydration, corrected for the patient's age (short: relAEOH, stated in liter [L/L], or without dimension) interpolation in treatments without a body composition measurement (short: BCM).

The informative value of the data available is limited by the small number of BCM measurements when compared to the data available for the Hb concentration. A new Hb value may be measured in every treatment from the blood volume monitor measurements (BVM), but new BCM data are only available about once a month. In order to increase time resolution it is possible to interpolate or extrapolate the OH between or from two BCM measurements by using changes in preweight (short: Prewgt), as in method 1, or changes in Hb (or HCT or BWC) as in method 2. These two methods are completely independent of each other.

In the first method, it is assumed that changes in preweight (short: Prewgt) are exclusively invoked by changes in OH, assuming patients have no residual renal function. In this assumption, different clothing and food in the stomach and intestine from day to day are neglected. It is believed that over longer time periods these errors will cancel out in the average and only increase the fluctuation around the true value.

Method 1 can also take into account changing trends in body composition by linearly interpolating the normoweight (computed as fat mass plus lean mass but without overhydration (OH, in mass or liter)) between two BCM measurements. The present or later overhydration OH2 can then be calculated from the difference between preweights Prewgt1 and Prewgt2 plus the earlier overhydration OH 1.

Method 1 (not taking into account body composition or normoweight):

$$OH2 = OH1 + (Prewgt2 - Prewgt1) \quad (1)$$

In the second method, the overhydration OH2 is calculated from relative changes in pre-dialysis Hb (or hematocrit HCT, or blood water content BWC), which translate directly into changes of ECW. Please note that the same relative changes in ECW and in blood volume (i.e., a constant Guyton factor) is assumed.

Method 2:

$$ECW1/ECW2 = Hb2/Hb1 => ECW2 = ECW1 * Hb1/Hb2 \quad (2)$$

$$OH2 = OH1 + ECW2 - ECW1 = OH1 + ECW1 * (Hb1/Hb2 - 1) \quad (3)$$

In these equations (with the equations being examples for mathematical relations within the meaning of the present invention), index 1 denotes the last or earlier measurement, and index 2 denotes the new or missing or later value. OH1, Prewgt1 and Prewgt2, Hb1 and Hb2 (or HCT1 and HCT2) have to be known in order to calculate the new OH2.

FIG. 1 gives an example of these interpolations. The dots 1 inside the circles 3 indicate true body composition (BCM) measurements of relAEOH. The empty circles 3 represent results obtained from interpolation method 1 (based on preweights). The crosses 5 reflect results for relAEOH obtained from method 2 (Hb1/Hb2 interpolation). One can see that both methods give slightly different results and trends, because the underlying assumptions are not fully met (e.g., for method 2 no significant change in the mass of haemoglobin (short: mass_Hb) is assumed). Method 1 can be further improved by taking into account changing trends in the normoweight (=lean mass+fat mass, without the weight of the overhydration OH).

Of course, these methods 1 and 2 are not only applicable for interpolation between two known values for OH, but also for extrapolation in which only an older or earlier OH is given but new or later preweights or Hb measurements are available.

FIG. 1 shows the relAEOH interpolation over time (for months July (07) of one year to January (01) of the following year) by methods 1 (circles 3) and 2 (crosses 5). The dots 1 indicate true OH measurements from the BCM. The circles 3 reflect the relAEOH values interpolated from preweight. The dots 1 reflect the relAEOH measurements by means of the body composition (BCM) monitor. Those measurements did only take place about once a month. The crosses 5 reflect the relAEOH values calculated from Hb. Hb was available for every treatment session.

Figure 2:
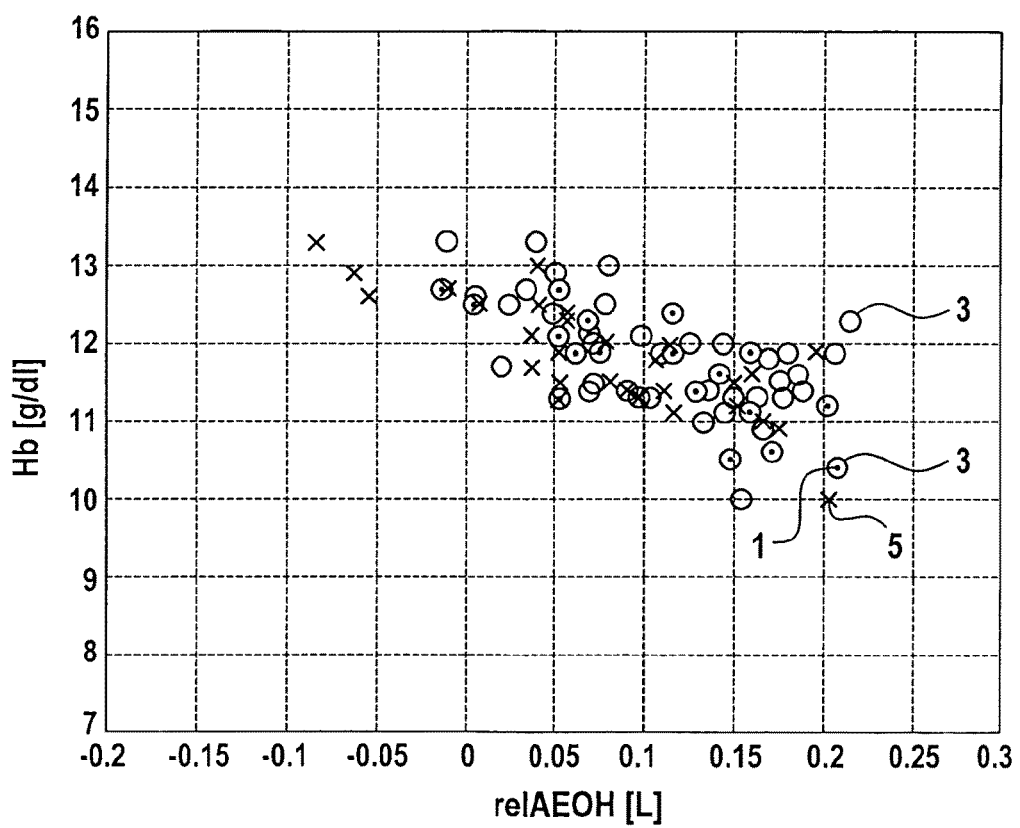
FIG. 2 shows the additional information of the interpolated data of FIG. 1 in a Hb-over-OH-plot.

FIG. 2 shows the additional information of the interpolated data in a Hb-over-relAEOH-plot. It is not as precise as a plot comprising only data from direct BCM measurements, but gives more data points with standard data from the clinics. Besides, no additional device or measurement is needed to arrive at the plot of FIG. 2.

As in FIG. 1, the dots 1 reflect the relAEOH measurements by means of the body composition (BCM) monitor, the circles 3 reflect the relAEOH values interpolated from preweight and the crosses 5 reflect the relAEOH values calculated from Hb.

Having two estimations for the new (or later) OH value from methods 1 and 2, it is possible to perform a weighted averaging of these two values in respect to their uncertainties in order to increase precision. For example, one can take ⅓ of OH2_method 1 and ⅔ of OH2_method2. However, there is yet another way to combine both methods to interpolate OH, taking into account the measurement uncertainties.

Figure 2A:
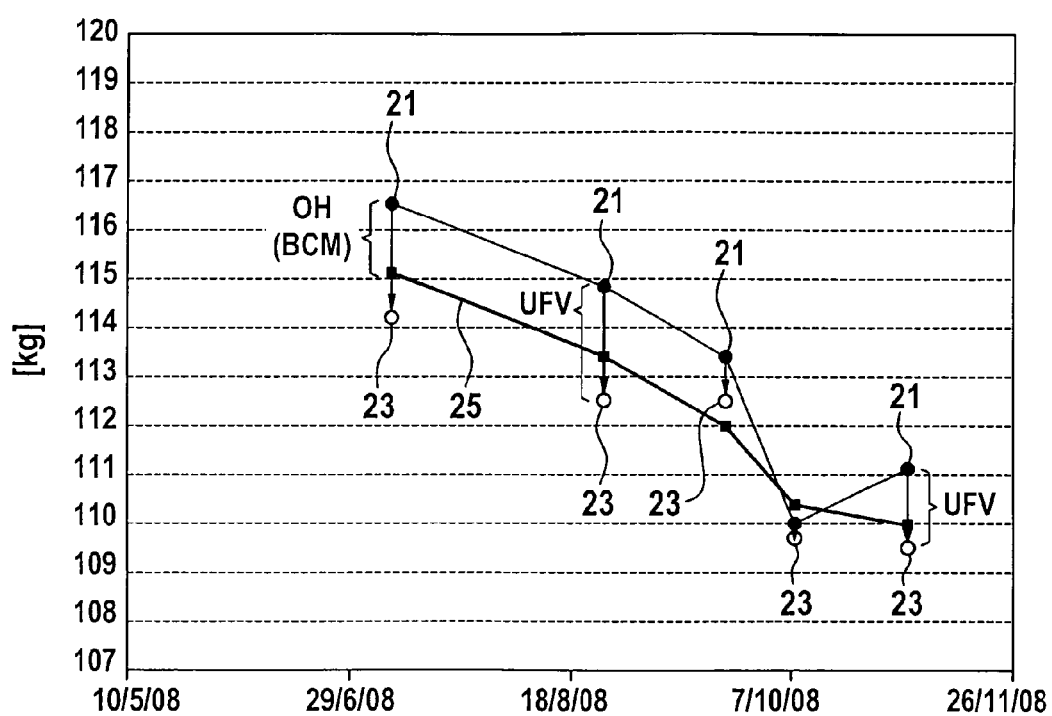
FIG. 2a shows another interpolation method according to the present invention.
Figure 2B:
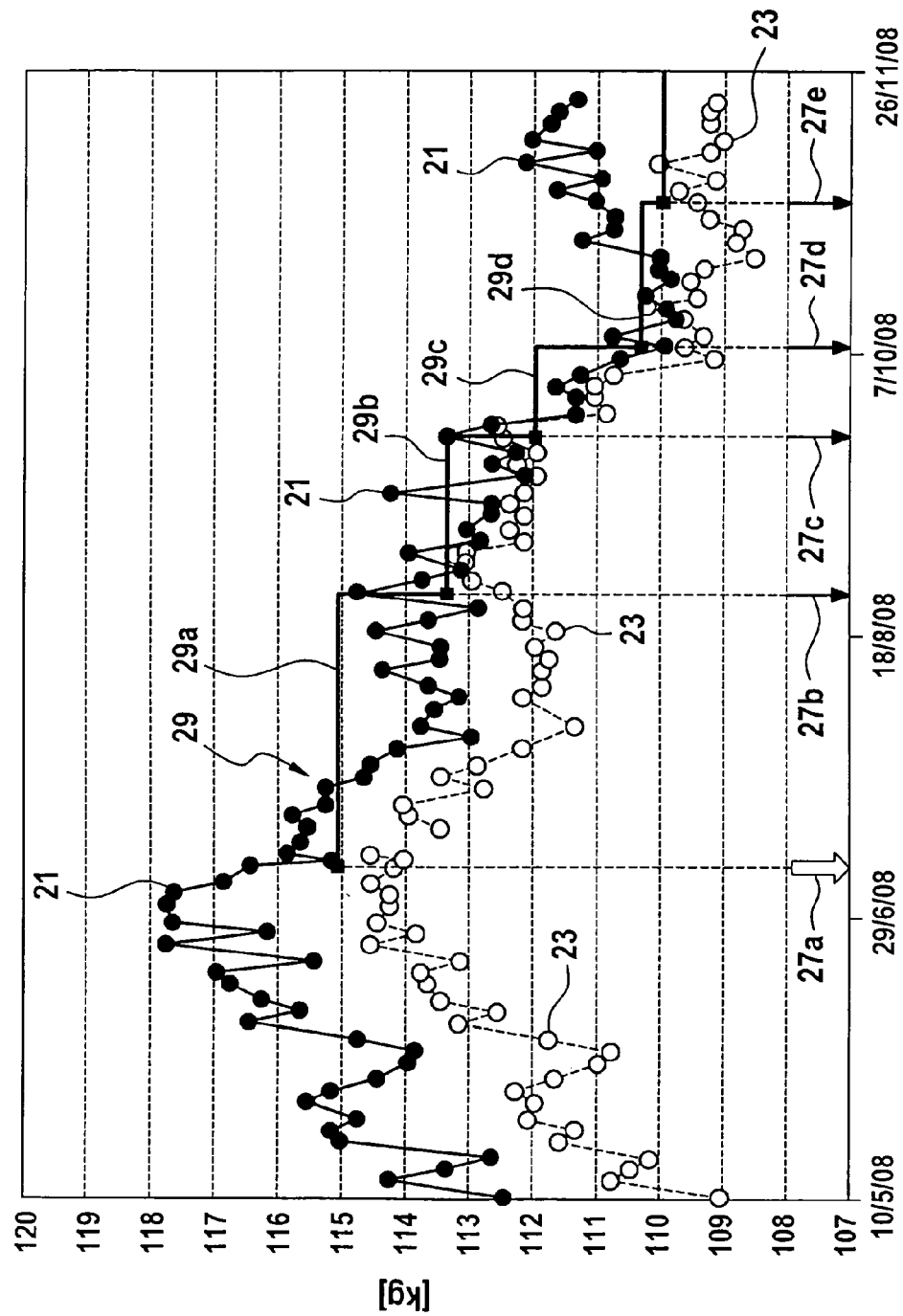
FIG. 2b shows yet another interpolation method according to the present invention.
Figure 2C:
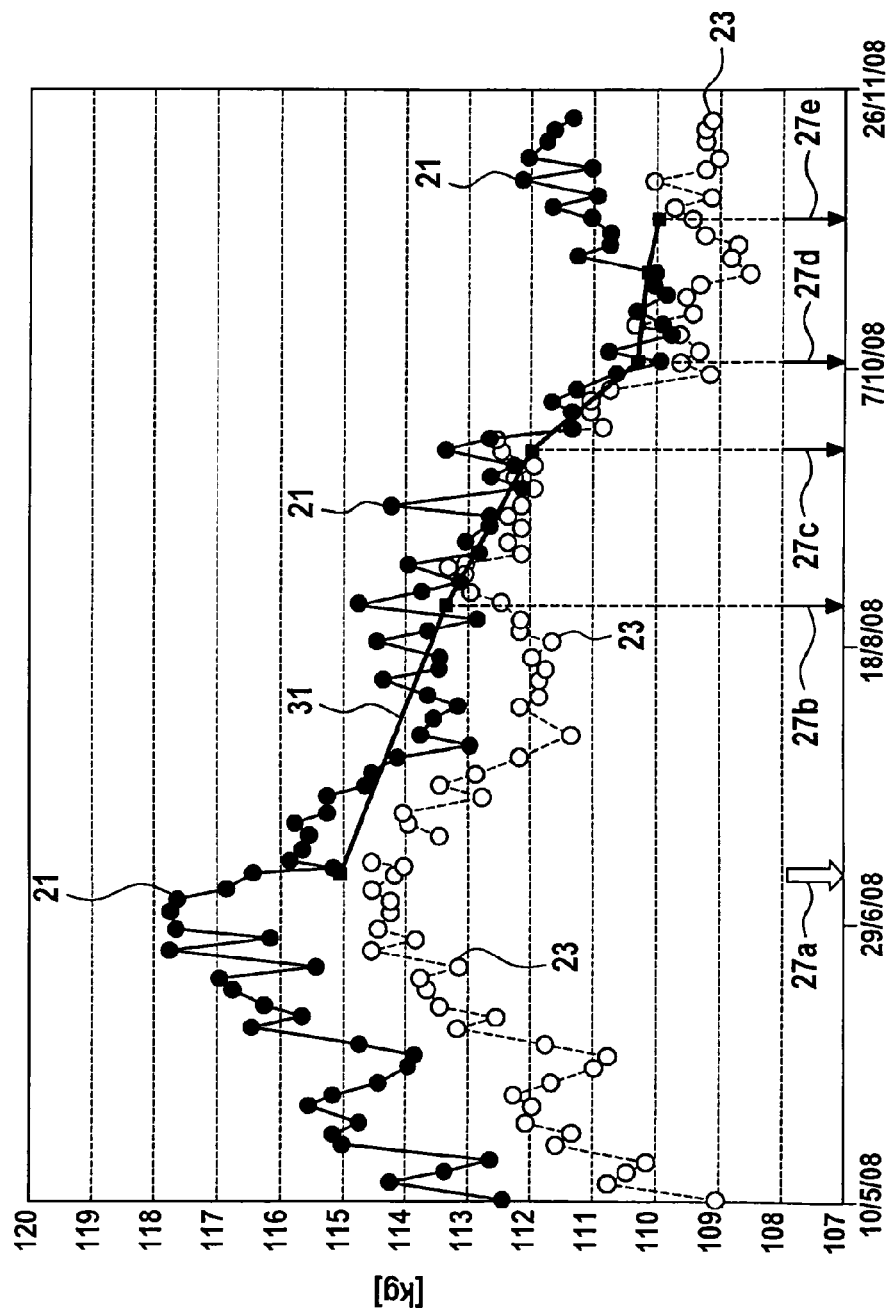
FIG. 2c shows yet again another interpolation method according to the present invention.

Above interpolation methods can be refined as is discussed with regard to FIGS. 2a to 2c.

FIG. 2a helps understand the interpolation methods explained below. As FIGS. 2b and FIG. 2c, FIG. 2a illustrates the weight in [kg] of the patient over time. In particular, the dark circles 21 represent the preweight of the patient on days on which body composition measurements have been made before dialysis; the hollow circles 23 represent the postweight of the patient after dialysis. Of course, a number of additional treatments have been carried out between the day on which an BCM measurement has taken place besides the blood treatment. Only, for enhanced understanding, data from those treatments are not illustrated in FIG. 2a. They are, however, illustrated in FIGS. 2b and 2c. In FIG. 2a, the effect of the ultrafiltration volume UFV on the patient's weight can be seen—it equals the difference between preweight and postweight. Further, the overhydration level OH as measured by the BCM measurement is indicated. Curve 25 links the findings for the overhydration of each of the five BCM measurements. Hence, curve 25 reflects the normohydrated weight (i.e., at OH=0 L, that is the weight composed of the LTM and ATM, and also the weight of the patient before treatment (preweight) minus any overhydration OH). Curve 25 allows for an interpolation of the overhydration. It appears that the fourth BCM measurement is incorrect.

In contrast to FIG. 2a, FIG. 2b shows additional preweight data 21 and postweight data 23 of every single dialysis treatment carried out between May 2008 and November 2008. The interpolation procedure shown in FIG. 2b starts at the first BCM measurement indicated by arrow 27a. Starting from the value of the normoweight (approx. 115 kg) obtained by means of the first BCM treatment, a horizontal line 29a is drawn until a second normohydrated weight is known from following measurement indicated by arrow 27b. The second normohydrated weight obtained in August 2008 is the starting point of another horizontal line 29b that extends from the second arrow 27b to the third arrow 27c (fourth and fifth arrows 27d and 27e indicate fourth and fifth measurements). Lines 29a, 29b, 29c and 29d can be understood as individual steps of a step arc 29. Now, the overhydration of any treatment day may be interpolated by calculating the difference between any preweight at issue and the height or value of the corresponding line 29a, 29b, 29c, or 29d of the step arc 29.

FIG. 2c shows yet another interpolation method. This method differs from the one discussed with regard to FIG. 2b in that no step-like interpolation is contemplated. Rather, any normohydrated weight obtained by means of a BCM measurement is connected to the subsequent one by means of a straight line 31. That way, a linear interpolation of the normoweights is achieved. A particular interpolated value of the overhydration present on a particular day is calculated as the difference between the preweight of the patient and the corresponding section of line 31 that relates to the day and preweight at issue.

The method shown in FIG. 2c differs from that of FIG. 2b in that any change of the body composition taken place since the last BCM measurement (that is, any change in the ratio of LTM to ATM or any change in either LTM or ATM) may be detected or reflected as such. It is hence one advantage of the method of FIG. 2c that changes in preweight are not falsely interpreted as changes in overhydration if they do not relate to those.

By extending line 31 beyond the latest overhydration measurement (which assumes that the change in body composition continues at the same rate) it is possible to extrapolate the overhydration into the future (in respect to the latest OH measurement). For example, for every new preweight coming in, the difference between the new preweight and the extended line 31 resembles the extrapolated overhydration.

The advantages of both interpolation methods 1 and 2 (see also equations (1) to (3) and the corresponding explanations) can be combined in an optimal way by using a mathematical filter, for example the so-called Kalman filter, which uses all available information to calculate the most likely value of an inner state variable. This application will be explained in the following.

The Kalman filter is a recursive filter based on a state space model representation of a system named after Rudolf Kalman. Its purpose is to use measurements that are observed over time that contain noise (random variations) and other inaccuracies, and produce values that tend to be closer to the true values of the measurements and their associated calculated values.

The Kalman filter produces predictors or estimates of the true values of parameters and their associated calculated values by predicting a value, estimating the uncertainty of the predicted value, and computing a weighted average of the predicted value and the measured value. The most weight is given to the value with the least uncertainty. The estimates produced by this method according to the present invention tend to be closer to the true values than the original measurements because the weighted average has a better estimated uncertainty than either of the values that went into the weighted average. For example, in one exemplary embodiment of the present invention, one has five state variables x1(k) to x5(k), k being the time step (in this example: days), assembled in the state vector x(k), the state variables being:

i) normo-hydrated blood volume $BV_0$
ii) mass of haemoglobin mass_Hb
iii) overhydration OH
iv) Guyton factor $K_{Guyton}$ which defines the relation between blood volume and ECW as follows:

$$BV=BV_0+OH/K_{Guyton}.$$

A normal range for $K_{Guyton}$ is between 3 and 20.
v) Normoweight (or normweight, short: Normwgt, being the body weight at zero overhydration)

These five state variables are set into relation by two means: a) the transition matrix A, which determines how the states of the next time step depend on the previous states, and b) the output matrix, which determines how the inner states relate to the measurements. The original formulation of the Kalman filter was made only for linear systems. Since the system of this exemplary embodiment is nonlinear, a so-called extended Kalman filter algorithm (EKF) is used which includes a linearization procedure. Furthermore the Kalman filter can be used in a forward-backward way, so that for all retrospective data the 'known future' is also taken into account and the states do not suddenly jump to a new measurement, but rather start moving towards the 'next measurement' earlier.

Figure 3:
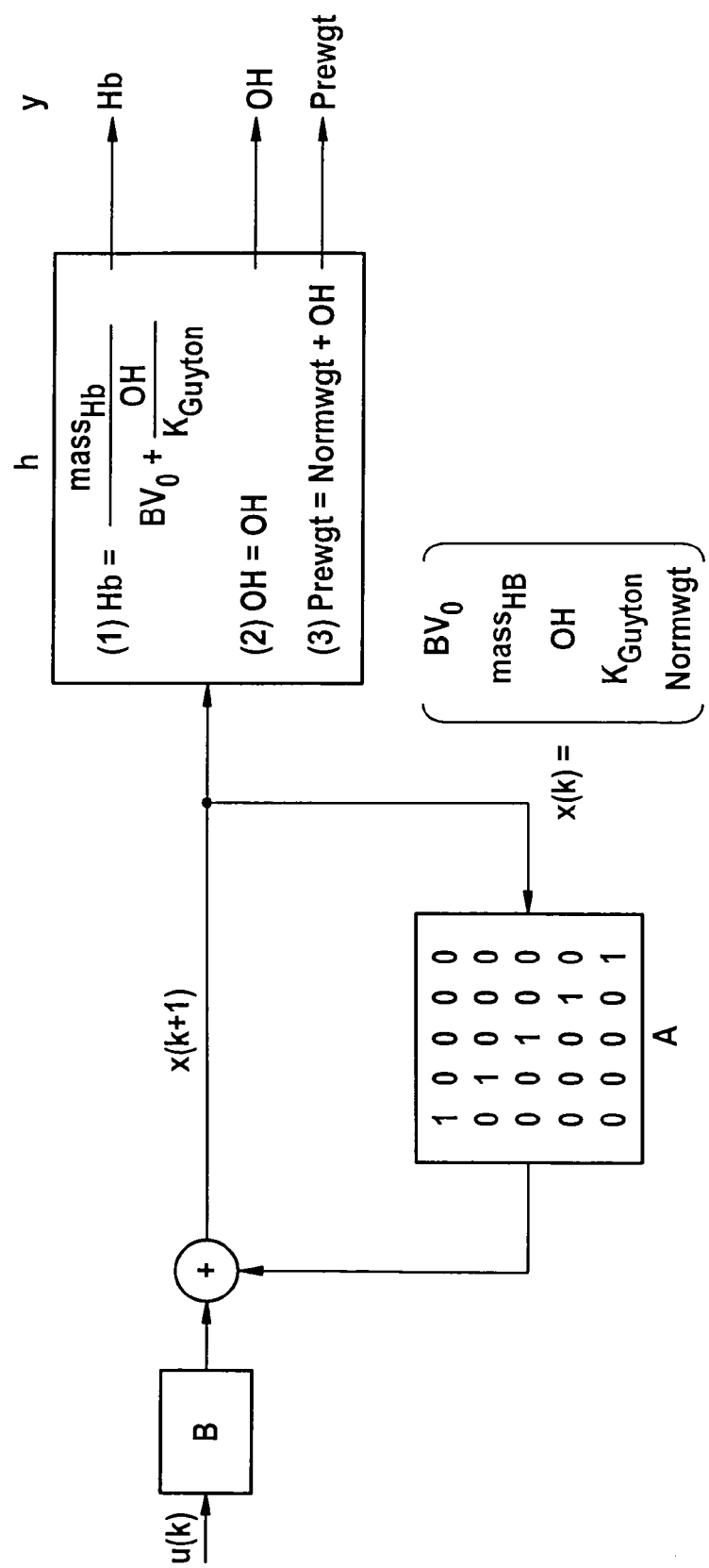
FIG. 3 shows the structure of a discrete Kalman filter, including output equations.

The structure of this system is shown in FIG. 3. An important part is the biological model represented in observation matrix h comprising the output equations (the output equations being examples for mathematical relations within the meaning of the present invention). In addition to these model equations of the observation matrix h, the Kalman filter uses knowledge about the measurement uncertainty and inner state variability to calculate optimal updates of the inner states at every new time step, even if one of the measurements is missing. In one exemplary embodiment, the following uncertainties (in terms of ±standard deviation) are used, which are provided to the Kalman filter in the so called 'covariance matrices':

Measurement noise (in +−SD)
Hb±0.5 g/dl
OH±0.5 L
Prewegt±0.5 kg
Process uncertainty:
$BV_0$±0.1 L
mass_Hb±50 g
OH±0.5 L
$K_{Guyton}$±0.1
Normwgt±0.2 kg Above uncertainties and assumptions for noise have been found based on reference values and observations. Other assumptions for uncertainty and noise than the ones stated above may be contemplated as well, of course.

FIG. 3 shows the structure of the discrete Kalman filter, including the output equations h. The transition matrix A simply passes on the last state variables x(k) to the next step k+1 [x(k)=A*x(k−1)+B*u(k)+w(k)]. The vector u(k) is the input (could be EPO or iron dose but is not necessarily used), y is the output vector of the (inner state) variables that can be measured, and w is normally distributed Gaussian noise with zero mean.

x=Ax+Bu+w; meaning the state vector x evolves during one time step by premultiplying by the 'state transition matrix' A. There is optionally (if nonzero) an input vector u which affects the state linearly, and this linear effect on the state is represented by premultiplying by the 'input matrix' B. There is also Gaussian process noise w.

y=hx+v; meaning the observation vector y is a linear function of the state vector, and this linear relationship is represented by premultiplication by "observation matrix" h. There is also Gaussian measurement noise v.

where w~N(0,Q); meaning w is Gaussian noise with covariance Q v~N(0,R); meaning v is Gaussian noise with covariance R In the nonlinear case, which applies to our model, y is a function of the inner state variables $$x:y=h(x)+v.$$

'k' may stand for a specific (dialysis) treatment session. If no measurements are available for a parameter at the time 'k', in certain exemplary embodiments, the standard deviation may be switched for this parameter to an unusually high value. Doing so, the filter will not use the available, older values too much because of the high uncertainty. Other ways to proceed are of course also contemplated.

An implementation of the idea described herein may be embodied by means of the well known Matlab toolbox (see, e.g., http://www.lce.hut.fi/research/mm/ekfukf/).

It is to be noted that above example is not intended to limit the present invention in any way. Of course, more or less equations than the ones described above may be used.

One advantage provided for by the Kalman filter is that if no new measurement is available, or if only two out of three variables are measured at time k, then Kalman uses an inner prediction of the missing variable for the next time step. Therefore, this filter is optimally suited for interpolating data, since every new input improves the estimation, and noise is always taken into account. Only, explicit equations of the physiological system are needed to set up the filter. If the equations are known, and also the noises, then Kalman gives an optimal state estimation.

If, for example, a variable like mass_Hb can not be measured directly, by utilizing all data and the three output equations the filter calculates the most likely value for the mass.

So Kalman has two further advantages. Firstly, it serves as an optimal interpolator/extrapolator for all inner state variables including OH since all measurements are integrated in an optimal way. Secondly it calculates estimations of variables like mass_Hb which cannot be determined directly.

Figure 4A:
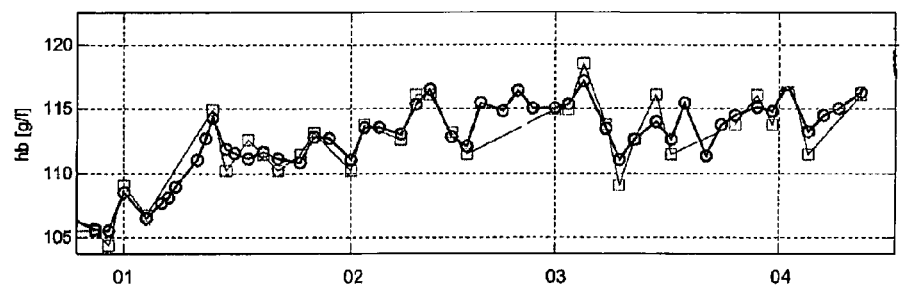
FIGS. 4a, b, c give an example of the interpolation according to the present invention in three variables (haemoglobin, overhydration and preweight).
Figure 4B:
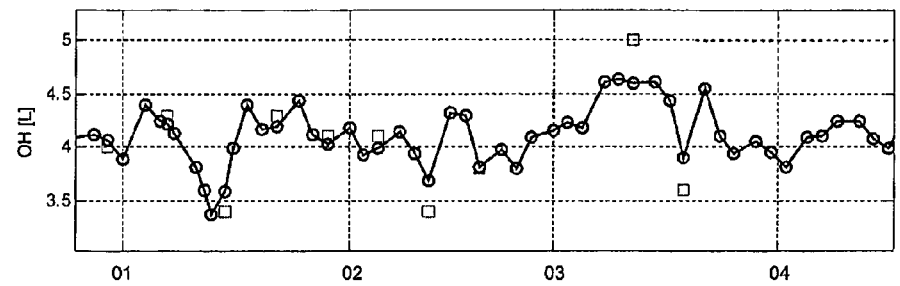
Figure 4C:
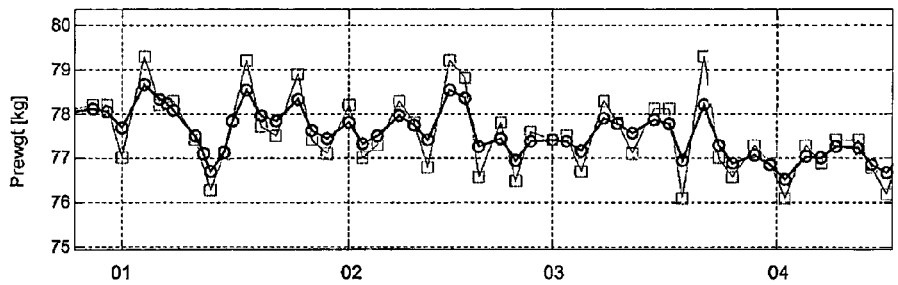

FIGS. 4a, 4b and 4c give an example of the interpolation in three variables (Hb, OH and preweight (short: Prewgt)). Please note that the true values are not exactly met by the Kalman filter, since it assumes some noise on the measurements and corrects for the noise accordingly.

FIG. 4a shows true predialysis Hb values, obtained from body volume measurements (BVM) as depicted by the squares in FIG. 4a. FIG. 4a further shows estimated predialysis Hb values obtained by using Kalman forward-backward-smoothening, as depicted by the circles shown in FIG. 4a.

FIG. 4b shows true overhydration data, obtained from body composition measurements (BCM) as depicted by the squares in FIG. 4b. FIG. 4b shows also estimated overhydration OH values obtained by using Kalman forward-backward-smoothening, as depicted by the circles shown in FIG. 4b.

If, as is often the case, only preweight information is available for a blood treatment session, and if OH and Hb are missing, they can be interpolated or extrapolated with sufficient accuracy as is illustrated by FIGS. 4a and 4b. The OH interpolation shown in FIG. 4b reveals better results than methods 1 or 2 alone, since Kalman includes all available measurements into its estimation.

FIG. 4c allows a comparison between true preweight Prewgt measurements as depicted by the squares in FIG. 4c. For comparison, FIG. 4c shows also estimated preweight Prewgt values obtained by using Kalman forward-backward-smoothening, as depicted by the circles. Additionally, FIG. 4c reveals the normweight (or normoweight) of the patient, depicted by means of the diamonds standing on their tips.

FIGS. 5a-f show the inner states of the Kalman filter used for the examples of FIGS. 4a, b, c.

Figure 5A:
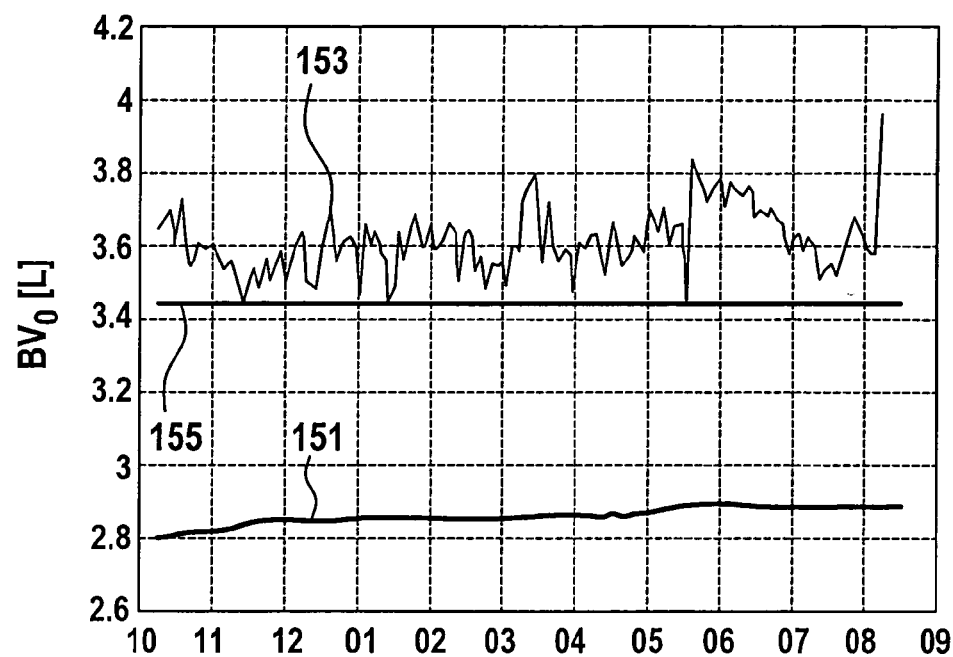
FIGS. 5a-f show the inner states of the Kalman filter used for the examples of FIGS. 4a, 4b, 4c.

For example, line 151 of FIG. 5a illustrates the blood start volume estimated by means of the Kalman filter. Curve 153 shows the real blood volume (calculated as: $BV_0+(OH/K\_Guyton)$). Line 155 states the start volume for $BV_0$ used for the filter.

Figure 5B:
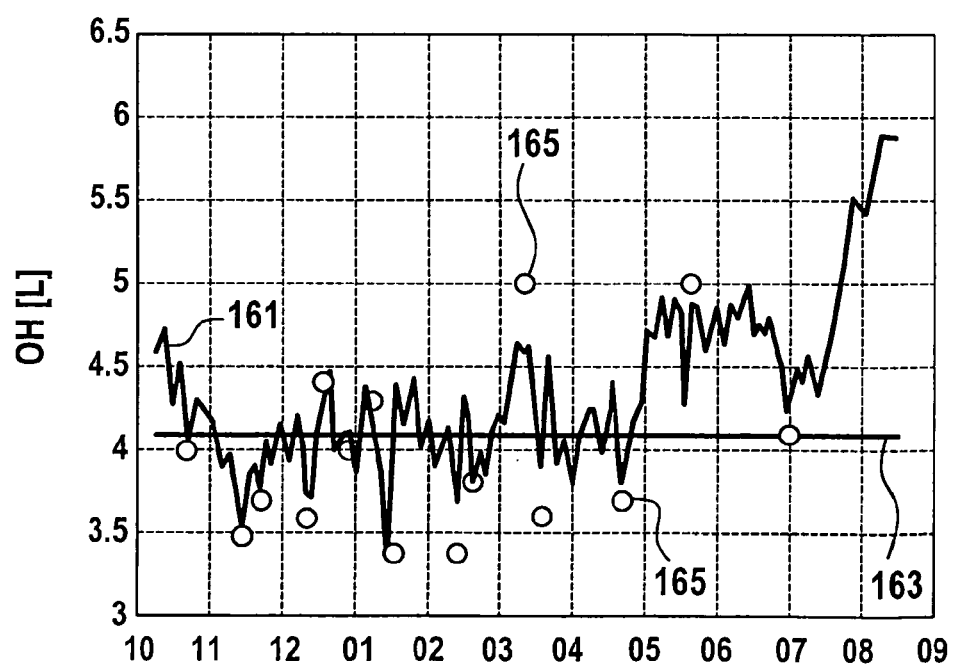

FIG. 5b illustrates the overhydration OH as estimated by means of the Kalman filter by curve 161. Curve 163 shows the value used for the overhydration as used for the filter. Circles 165 illustrate real values for overhydration as obtained by means of the body composition measurements (BCM).

Figure 5C:
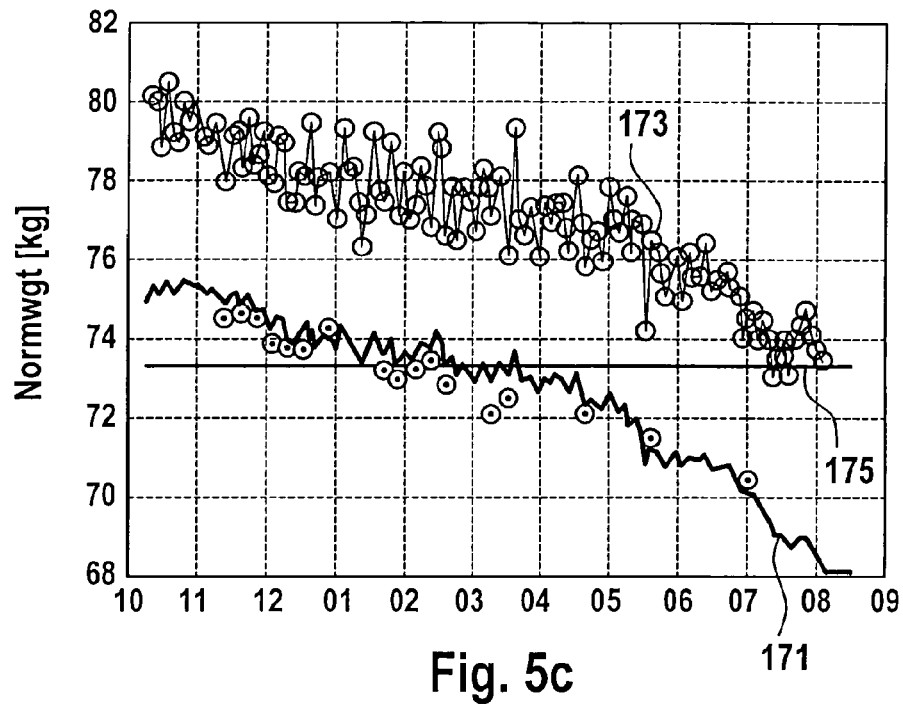

FIG. 5c illustrates the normoweight Normwgt as estimated by means of the Kalman filter by curve 171. Curve 175 shows the value used for the normoweight as used for the filter. The circles interconnected to curve 173 illustrate real values for the patient's weight obtained from weighting on a bascule.

Figure 5D:
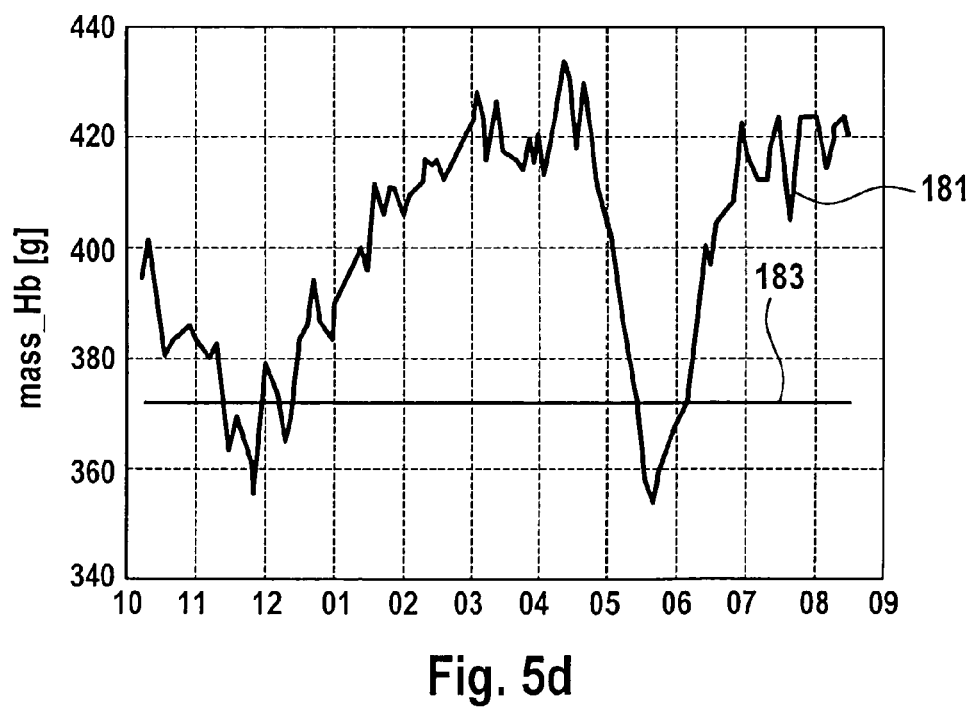

FIG. 5d illustrates the mass of haemoglobin mass_Hb as estimated by means of the Kalman filter by curve 181. Line 183 shows the value used for mass_Hb for needs of the filter.

Figure 5E:
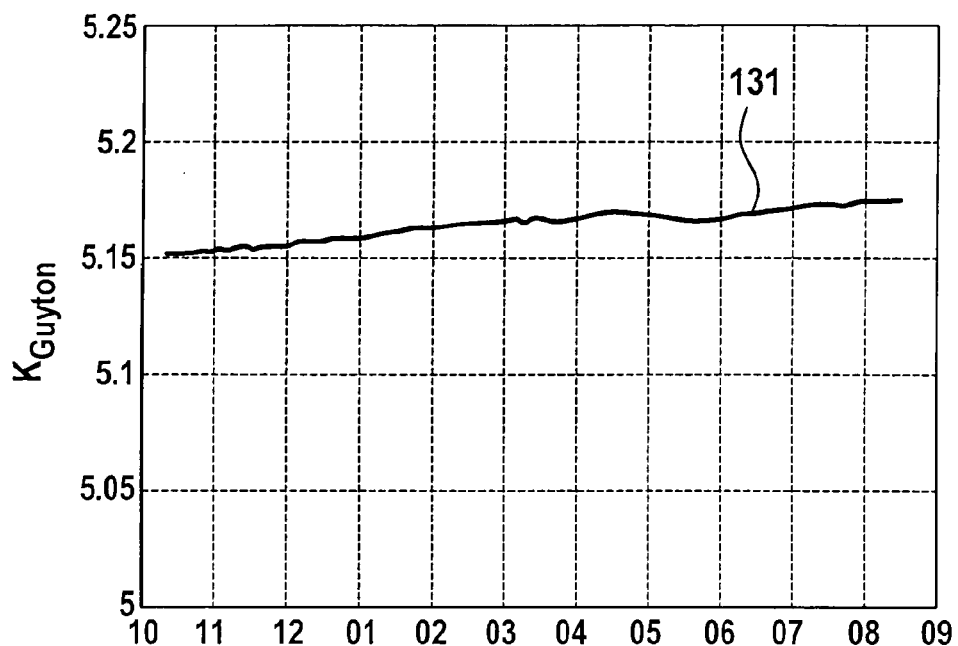

FIG. 5e illustrates the Guyton factor K_Guyton as estimated by means of the Kalman filter by curve 191.

Figure 5F:
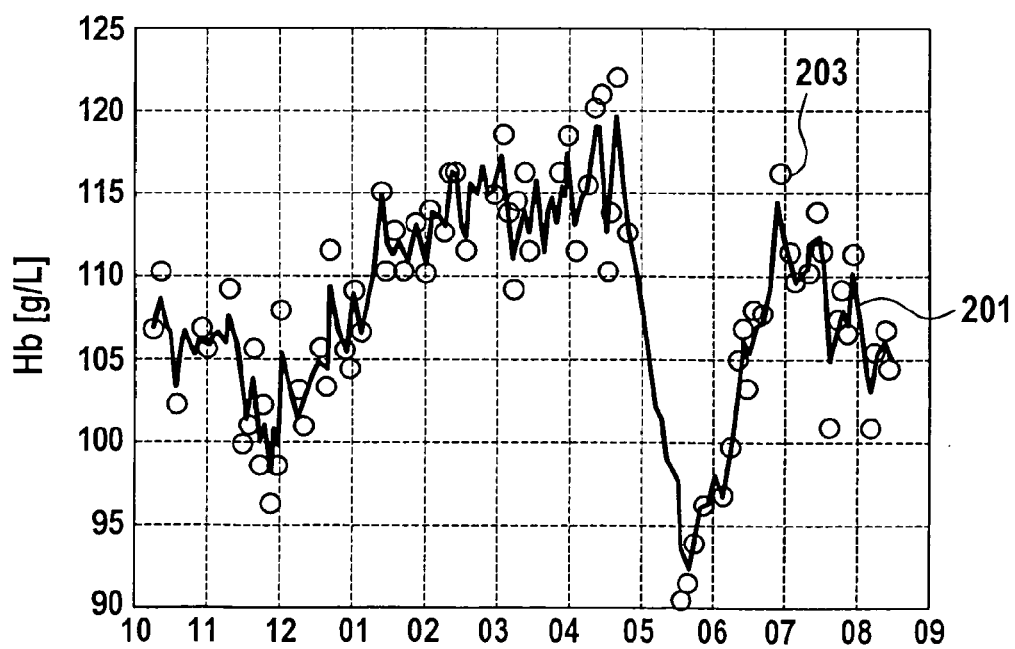

FIG. 5f illustrates the concentration of haemoglobin Hb as estimated by means of the Kalman filter by curve 201. Circles 203 illustrate real values for actually measured concentration values.

Figure 6:
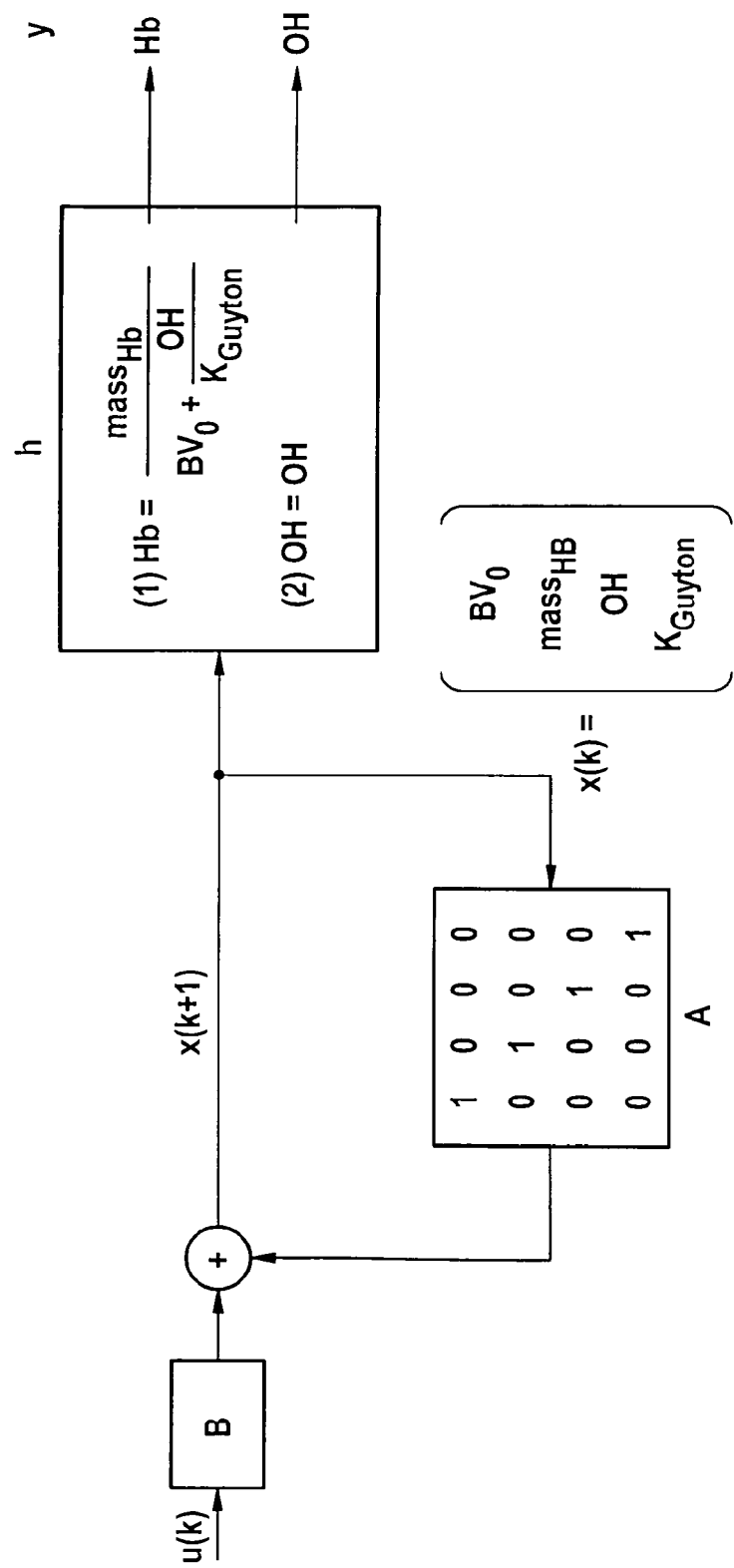
FIG. 6 shows another state space model with less inner states compared to that of FIG. 3.

FIG. 6 shows another state space model with less inner states compared to the model of FIG. 3. In the model of FIG. 6, the filter operates with one inner state less. As can be seen from FIG. 6, the normweight is no longer taken into consideration. In its remaining parts and aspects, the model of FIG. 6 is similar to that described above, in particular with regard to that of FIG. 3.

Figure 7:
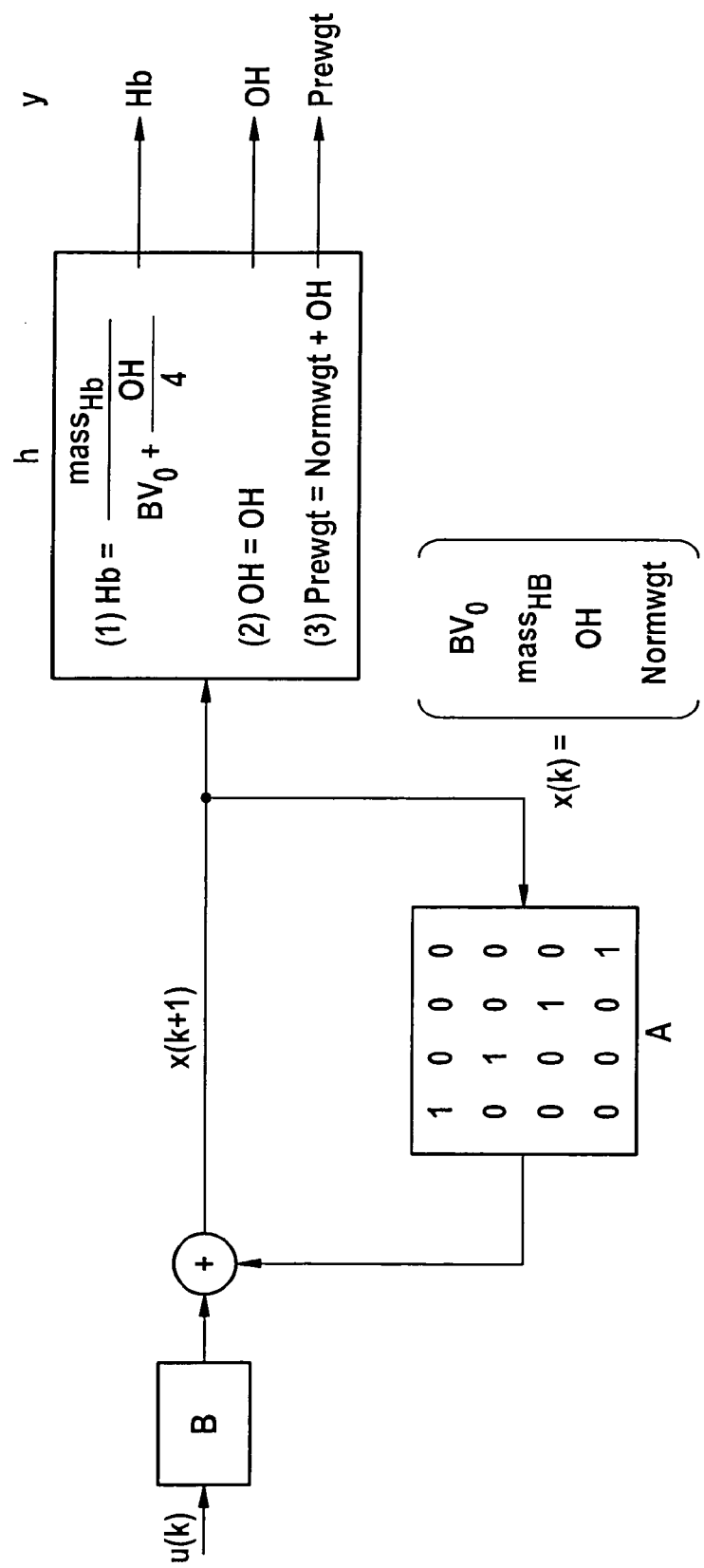
FIG. 7 shows yet another state space model like that of FIG. 3, simplified by assuming one factor as constant.

FIG. 7 shows yet another state space model like that of FIG. 3, simplified by assuming the Guyton factor as constant with K_Guyton being 4. Of course, K_Guyton may be constant at 3 or any other value considered as adequate.

Both the variations of the FIG. 6 and FIG. 7 allow at least for a quicker computation of the filter.

Figure 8:
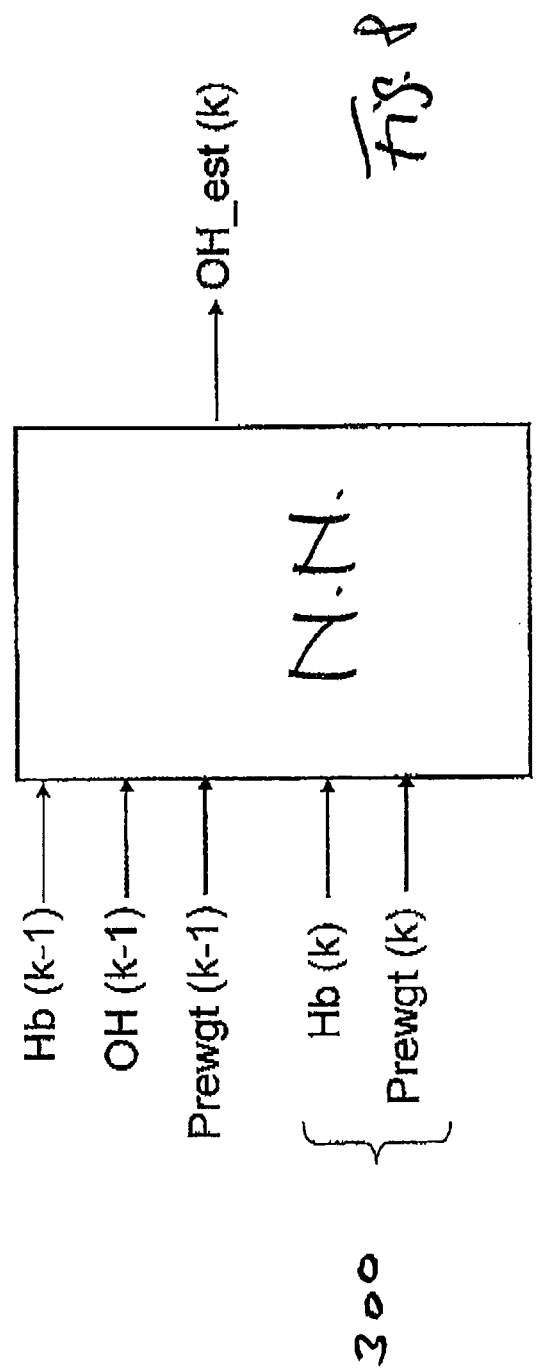
FIG. 8 shows the concept of a neuronal network in an exemplary embodiment according to the present invention.

FIG. 8 shows the concept of a neuronal network (short: N.N.).

Like the filter, in particular the Kalman filter, or the methods 1 and 2 as described above, neuronal networks can as well be used for estimating, interpolating or extrapolating missing values.

As can be seen from FIG. 8, the neuronal network N.N. shown there is configured for interpolating or extrapolating the overhydration OH. Hb and preweight Prewgt have to be measured or otherwise known.

As is obvious to the skilled person, using neuronal networks as in FIG. 8 is not at all limited to the interpolation or extrapolation of overhydration values. Rather, by simply exchanging input and/or output variable, for example the one depicted by reference numeral 300, other parameters than overhydration may be estimated by the neuronal network schematically shown in FIG. 8.

Besides, it is possible to consider not only the latest step (k−1) but also the latest but one step (k−2), and also even earlier steps than two steps behind.

Figure 9:
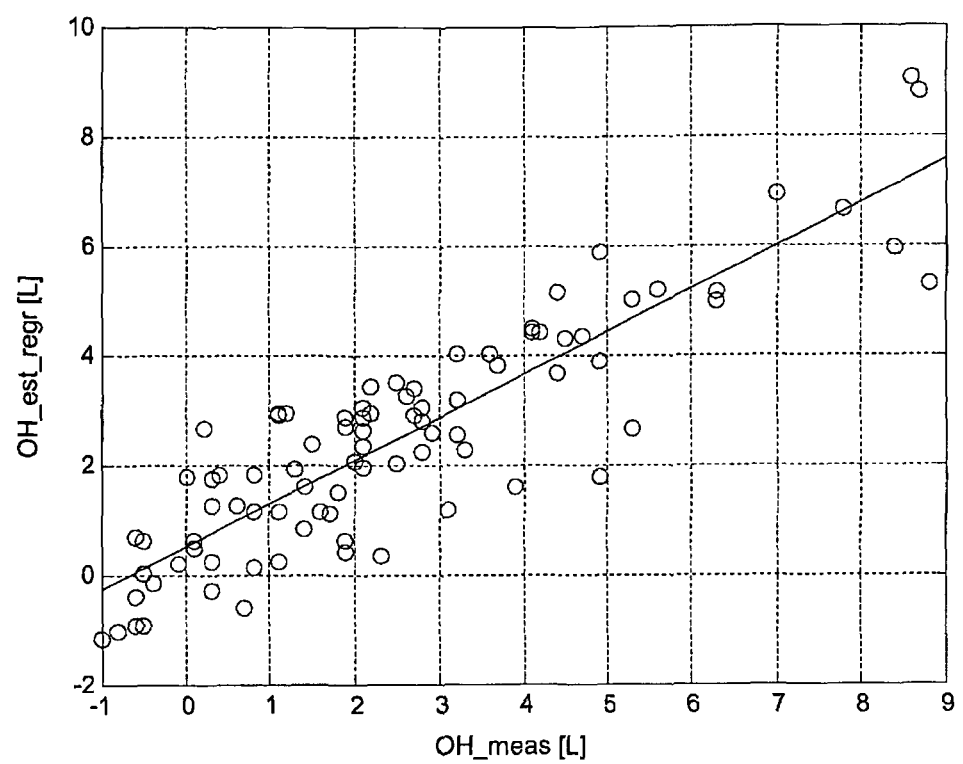
FIG. 9 shows the use of a simple regression equation to estimate the overhydration according to the present invention.

FIG. 9 shows the use of a simple regression equation $$OH\_est\_regr = a*BPsys + b*BPdia + c*Vena\_cava\_diameter\_pre\_max + d*OH(t-1) + e \qquad (4)$$

to estimate the overhydration according to the present invention. The regression analysis may also be used to inter-/extrapolate the overhydration OH. In FIG. 9, the correspondence between the overhydration status (OH_meas in [L]) measured by BCM (x-axis) and the overhydration OH_est_regr in [L] from equation (4) (y-axis) is easily noted. The data used for the illustration of FIG. 9 originated from a dryout study.

Parameters found by minimizing the sum of squared errors between the OH estimation and the measurement for all 86 data points of the dryout study were:

a=0.0510
b=−0.0362
c=0.1583
d=0.4129
e=−6.0463

BPsys and BPdia are measured before the treatment. OH(t−1) is the last measured OH, irrespective of how long ago it was measured. Vena_cava is the maximum diameter of the vena cava in [mm] Vena_cava may be measured by means of ultrasound or any other suitable imaging method.

Figure 10:
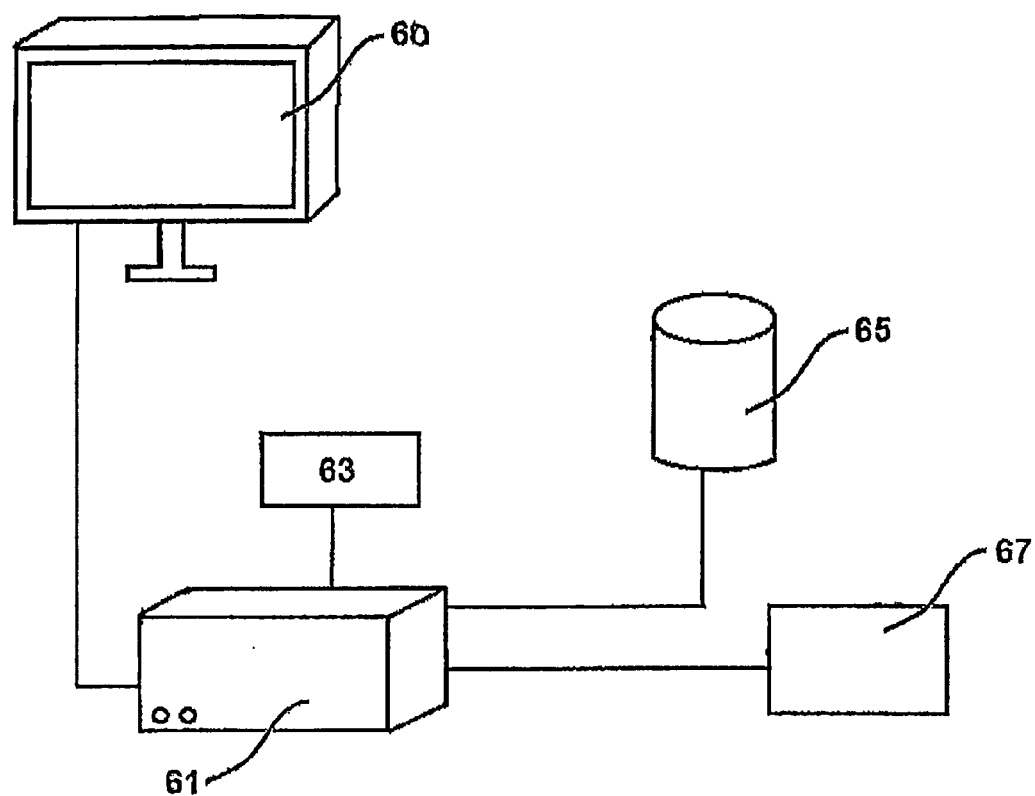
FIG. 10 shows a first apparatus comprising a controller for carrying out the method according to the present invention.

FIG. 10 shows an apparatus 61 comprising a controller 63 configured to carry out the method according to a first exemplary embodiment of the present invention. The apparatus 61 is optionally connected to an external database 65 comprising the results of measurements and the data needed for the method according to the present invention. The database 65 can also be an internal means of the apparatus 61. The apparatus 61 may optionally have means 67 for inputting data into the controller 63 or into the apparatus 61 itself. Such data may be information about the ultrafiltration rate set, the ultrafiltration volume planned to be eliminated from the body, etc., or approximations thereof. The results provided by the controller 63 and/or the apparatus 61 can be displayed on a monitor 60 or plotted by means of a—not displayed but optionally also encompassed in FIG. 10—plotter or stored by means of the database 65 or any other storage means. The database 65 can also comprise a computer program initiating the method according to the present invention when executed.

Figure 11:
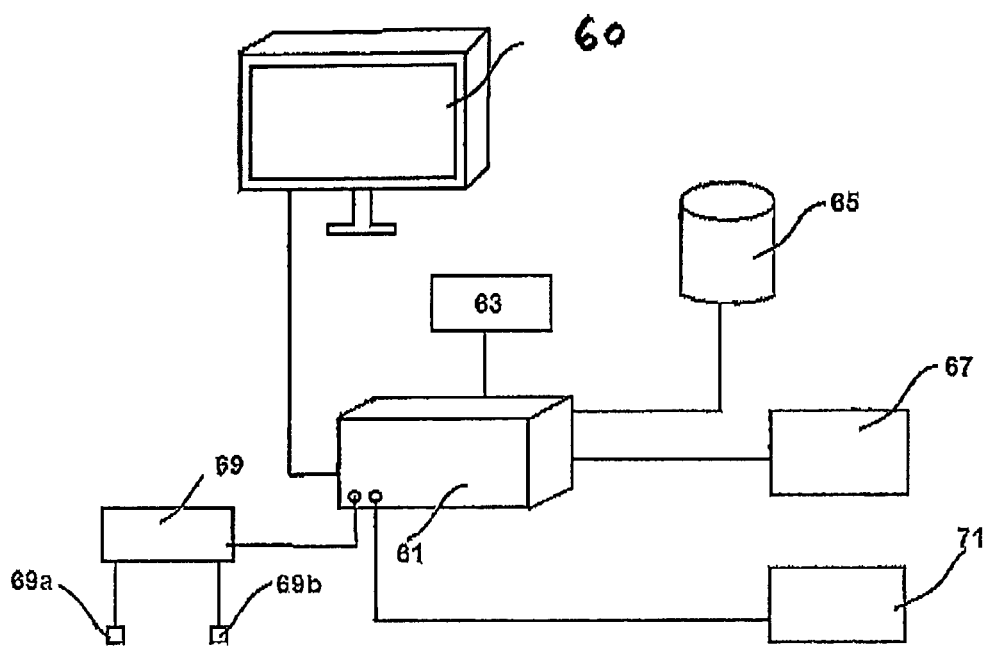
FIG. 11 shows a second apparatus comprising a controller for carrying out the method according to the present invention.

As can be seen from FIG. 11, for corresponding measurements, the apparatus 61 according to a second exemplary embodiment can be connected (by means of wires or wireless) with a bioimpedance measurement means 69 as one example of a means for measuring or calculating the overhydration, the lean mass, the fat mass or other parameters of the body or approximations thereof. Generally, the means for measuring or calculating can be provided in addition to the external database 65 comprising the results of measurements and the data needed for the method according to the present invention, or in place of the external database 65 (that is, as a substitute).

The bioimpedance measurement means 69 can be capable of automatically compensating for influences on the impedance data like contact resistances.

An example for such a bioimpedance measurement means 69 is a device from Xitron Technologies, distributed under the trademark Hydra™ that is further described in International Patent Publication No. WO 92/19153, the disclosure of which is hereby explicitly incorporated in the present application by reference.

The bioimpedance measurement means 69 may comprise various electrodes. In FIG. 7, only two electrodes 69a and 69b are shown which are attached to the bioimpedance measurement means 69. Additional electrodes are, of course, also contemplated.

Each electrode implied can comprise two or more ("sub"-)electrodes in turn. Electrodes can comprise a current injection ("sub-")electrode and a voltage measurement ("sub-")electrode. That is, the electrodes 69a and 69b shown in FIG. 11 can comprise two injection electrodes and two voltage measurement electrodes (i.e., four electrodes in total).

Generally spoken, the apparatus according to the present invention can be provided with means such as weighing means, a keyboard, a touch screen, etc. for inputting the required data, sensors, interconnections or communication links with a lab, any other input means, etc.

Similarly, the apparatus 61 may have further means 71 for measuring or calculating means for obtaining a value reflecting the overhydration and/or for obtaining values reflecting the mass, the volume or the concentration of Hb that can be provided in addition to the external database 65 or in place of the external database 65 (that is, as a substitute).

The means 71 can be provided as a weighing means, a keyboard, touch screen, etc. for inputting the required data, sensors, interconnections or communication links with a lab, a Hb concentration probe, any other input means, etc.

The invention claimed is:

1. A method of operating a blood treatment device for performing a blood treatment on a patient's blood, the method comprising:
   interpolating or extrapolating, by an interpolation or extrapolation device, at least one subsequent value of a first parameter indicative of an overhydration, a relative overhydration, or a normohydrated weight of the patient, taking into account:
      at least one earlier value of the first parameter obtained from a bioimpedance measurement device or from an external database during or before an earlier treatment session,
      at least one earlier value of a second parameter indicative of a preweight, a haemoglobin concentration in blood, or an extracellular water content and obtained from a bioimpedance measurement device or from an external database during or before the earlier treatment session,
      at least one subsequent value of the second parameter obtained after the at least one earlier value of the second parameter is obtained and before the treatment is performed, and
      a mathematical relation between the at least one earlier value of the first parameter, the at least one earlier value of the second parameter, and the at least one subsequent value of the second parameter; and
   performing, by the blood treatment device, the treatment in accordance to or based on the at least one interpolated or extrapolated subsequent value of the first parameter, the treatment comprising at least one of a dialysis treatment, a hemofiltration treatment, an ultrafiltration treatment, or a hemodialysis treatment.

2. The method according to claim 1, further comprising minimizing a mathematical error of the interpolating or extrapolating.

3. The method according to claim 1, further comprising minimizing a square error of the interpolating or extrapolating.

4. The method according to claim 1, further comprising weighting one or more of the earlier values.

5. The method according to claim 1, further comprising weighting values or mean values derived from earlier values of one or more parameters.

6. The method according to claim 1, further comprising using a mathematical filter, a regression analysis or neuronal networks.

7. The method according to claim 1, further comprising using a linear filter, a non-linear filter, a Kalman filter, an unscented Kalman filter, a Kalman-Bucy filter, a hybrid Kalman filter or an extended Kalman filter.

8. The method according to claim 1, further comprising using a filter that works partly or completely recursively.

9. An apparatus comprising a controller programmed to execute instructions to perform the steps of the method according to claim 1.

10. The apparatus according to claim 9, further comprising an output device for outputting results provided by carrying out the method.

11. The apparatus according to claim 9, wherein the controller is further programmed to execute instructions to control a device for treating a patient's blood in accordance with or based on the one or more values calculated or approximated or estimated by the method.

12. A blood treatment device, comprising at least one apparatus according to claim 9.

13. The device according to claim 12, wherein the controller is further programmed to execute instructions to treat a patient by means of dialysis.

14. The device according to claim 13, wherein the controller is further programmed to execute instructions to treat a patient by haemofiltration, ultrafiltration, and/or haemodialysis.

15. A non-transitory computer-readable storage medium with an executable program stored thereon, wherein the program instructs a programmable computer system so as to execute the steps of the method according to claim 1.

16. The method according to claim 1, further comprising outputting results of the method.

17. The method according to claim 1, wherein:
the treatment is a second treatment,
the at least one earlier value of the first parameter is obtained during a first treatment, and
the at least one subsequent value of the second parameter is obtained during the second treatment.

18. The method according to claim 1, wherein the at least one earlier value of the first parameter is obtained from the bioimpedance measurement device.

19. The method according to claim 1, wherein the treatment is a subsequent treatment, and the at least one earlier value of the second parameter is measured during an earlier treatment performed before the subsequent treatment.

* * * * *